(12) United States Patent
Figueredo et al.

(10) Patent No.: US 10,925,488 B2
(45) Date of Patent: Feb. 23, 2021

(54) INTRODUCED TO ELECTROMEDICAL EQUIPMENT FOR AUTOMATED TRIAGE OF NEWBORN WITH POSSIBLE CONGENITAL HEART DEFECTS

(71) Applicant: Hi Technologies SA, Curitiba (BR)

(72) Inventors: Marcus Vinícius Mazega Figueredo, Curitiba (BR); Sérgio Renato Rogal Júnior, Curitiba (BR); Marcelo Júnior Cossetin, Curitiba (BR); Raquel dos Santos Verríssimo, Curitiba (BR); Ricardo Alexandre Albuquerque Júnior, Curitiba (BR); Renan Nepomoceno Pinto, Curitiba (BR); Luan Ricardo Alves Pinheiro, Curitiba (BR); Hellen Christina de Carvalho, Piraquara (BR); Mayara Suelen Almeida dos Santos, Curitiba (BR); Renato Eleutério Siqueira, Curitiba (BR)

(73) Assignee: HI TECHNOLOGIES S.A., Curitiba (BR)

( * ) Notice: Subject to any disclaimer, the term of this patent is extended or adjusted under 35 U.S.C. 154(b) by 419 days.

(21) Appl. No.: 15/668,124

(22) Filed: Aug. 3, 2017

(65) Prior Publication Data

US 2018/0035890 A1 Feb. 8, 2018

(30) Foreign Application Priority Data

Aug. 4, 2016 (BR) ...................... 10 2016 018146 1

(51) Int. Cl.
*A61B 5/1455* (2006.01)
*A61B 5/00* (2006.01)
*A61B 5/0205* (2006.01)

(52) U.S. Cl.
CPC .......... *A61B 5/0011* (2013.01); *A61B 5/1455* (2013.01); *A61B 5/0205* (2013.01);
(Continued)

(58) Field of Classification Search
None
See application file for complete search history.

(56) References Cited

U.S. PATENT DOCUMENTS

2010/0030040 A1 2/2010 Poeze et al.
2011/0082711 A1 4/2011 Poeze et al.

FOREIGN PATENT DOCUMENTS

BR 9001119 A * 3/1991
BR 102012012062 A2 4/2015
(Continued)

*Primary Examiner* — Marjan Fardanesh
(74) *Attorney, Agent, or Firm* — Pilloff Passino & Cosenza LLP; Sean A. Passino; Rachel K. Pilloff

(57) ABSTRACT

The present patent refers to improvements introduced in electromedical equipment, applied to automated triage of newborn babies with purpose to detect possible congenital heart defects by means of little heart test, through dedicated software (DS) implanted in memory (1-G), georeference block (1-M), pendrive (3), external HD (4), energy and supply assembly (E) provided with DC02215V J4 connector, cable and power supply, plug (P) positioned at the rear panel of the apparatus (1), internal and external connections (C) with magnets arranged into two rows at the rear part of the apparatus (1), of "C"-shape metallic base (2) with two front flanges (2-A), aiming to increase the number of users, increase flexibility of test protocol and change the usability in order to minimize errors, bringing advantages of higher testing speed, improved interface with user, better measurement quality, lower cost, higher usage versatility, and lighter weight and smaller size of equipment.

3 Claims, 6 Drawing Sheets

Figure 1:
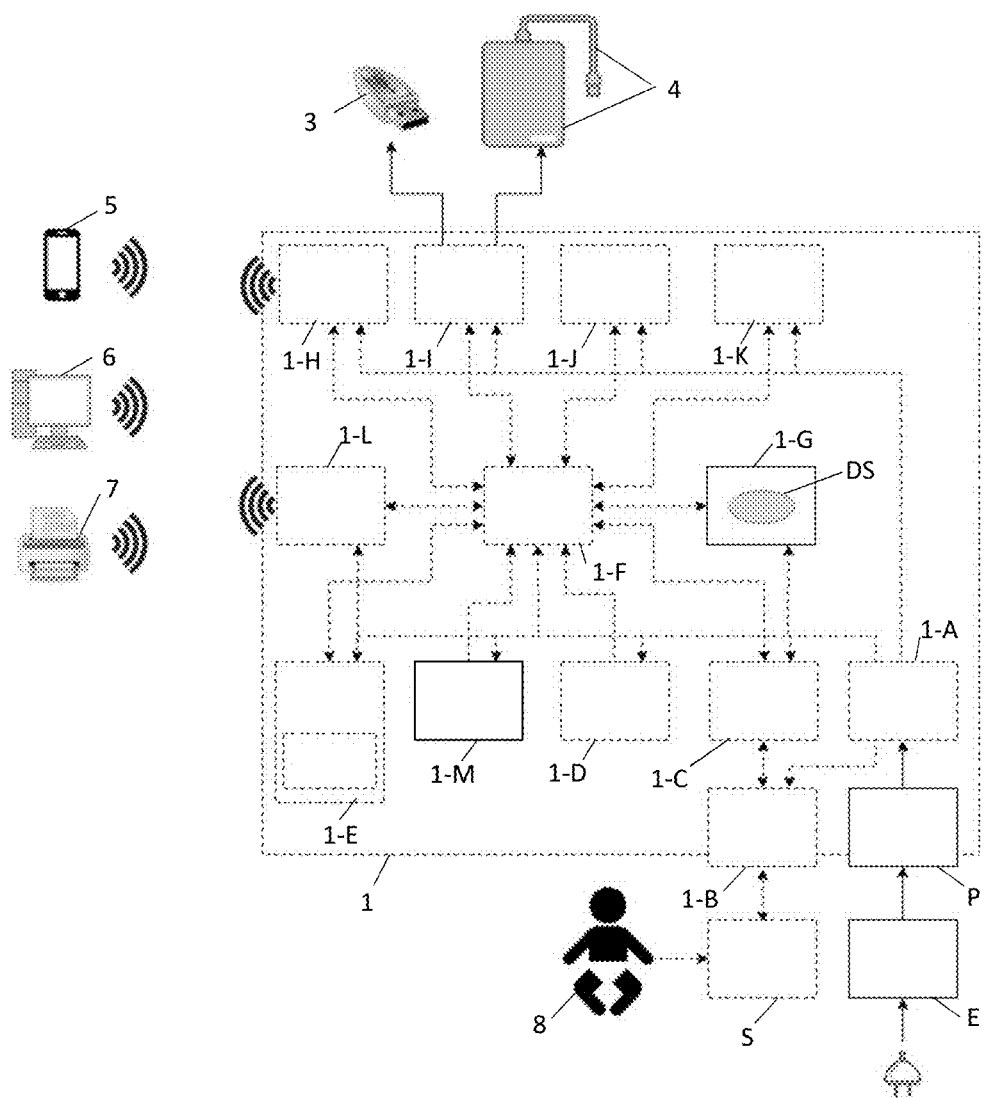
Figure 2A:
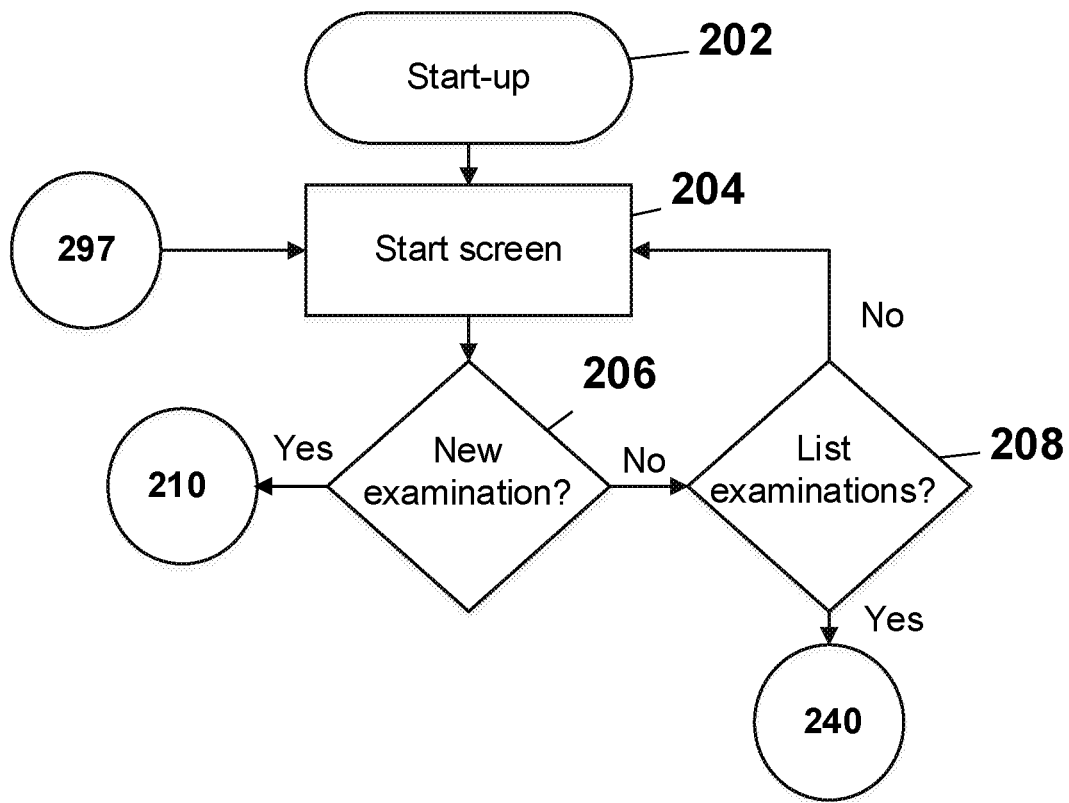
Figure 2B:
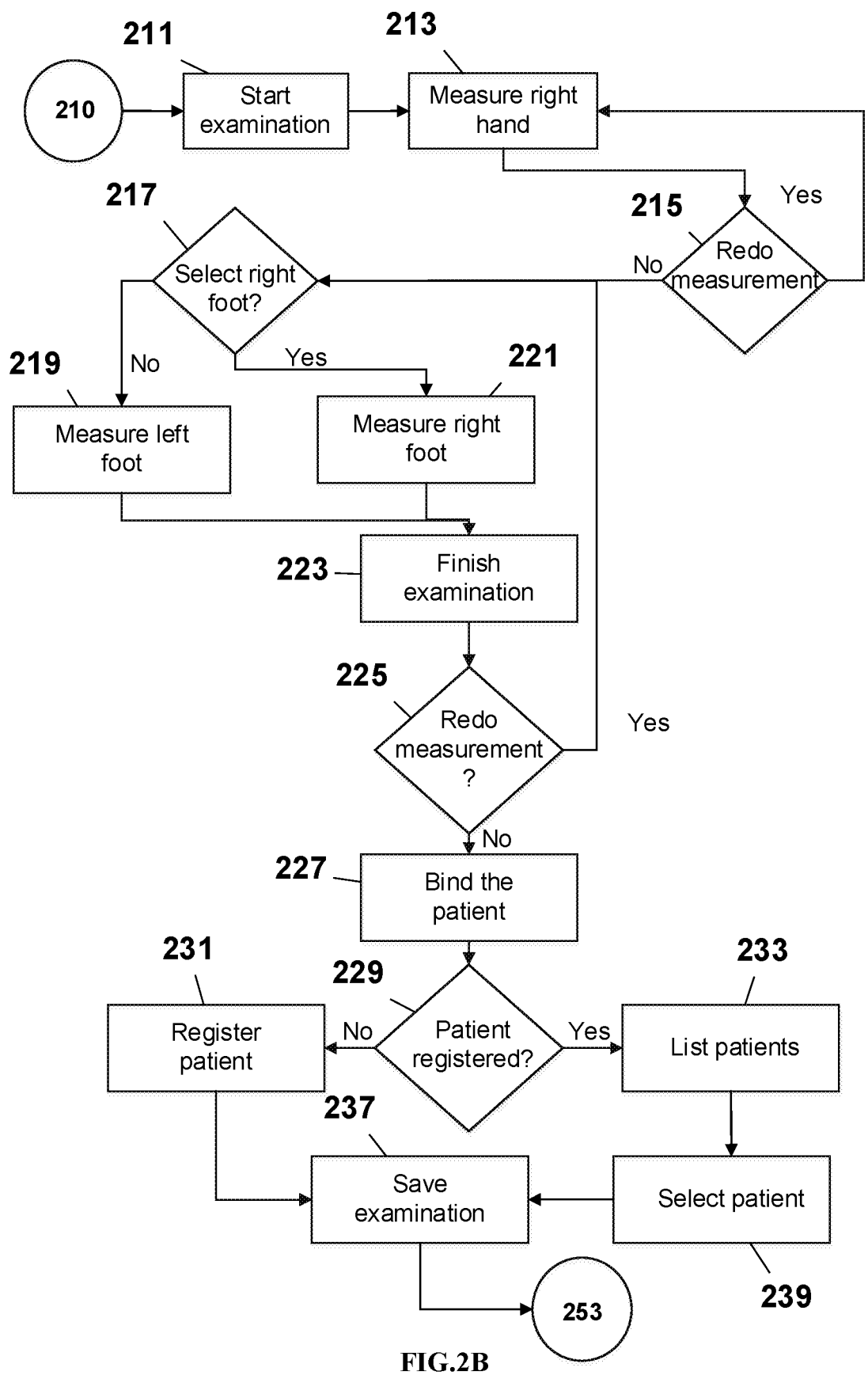
Figure 2C:
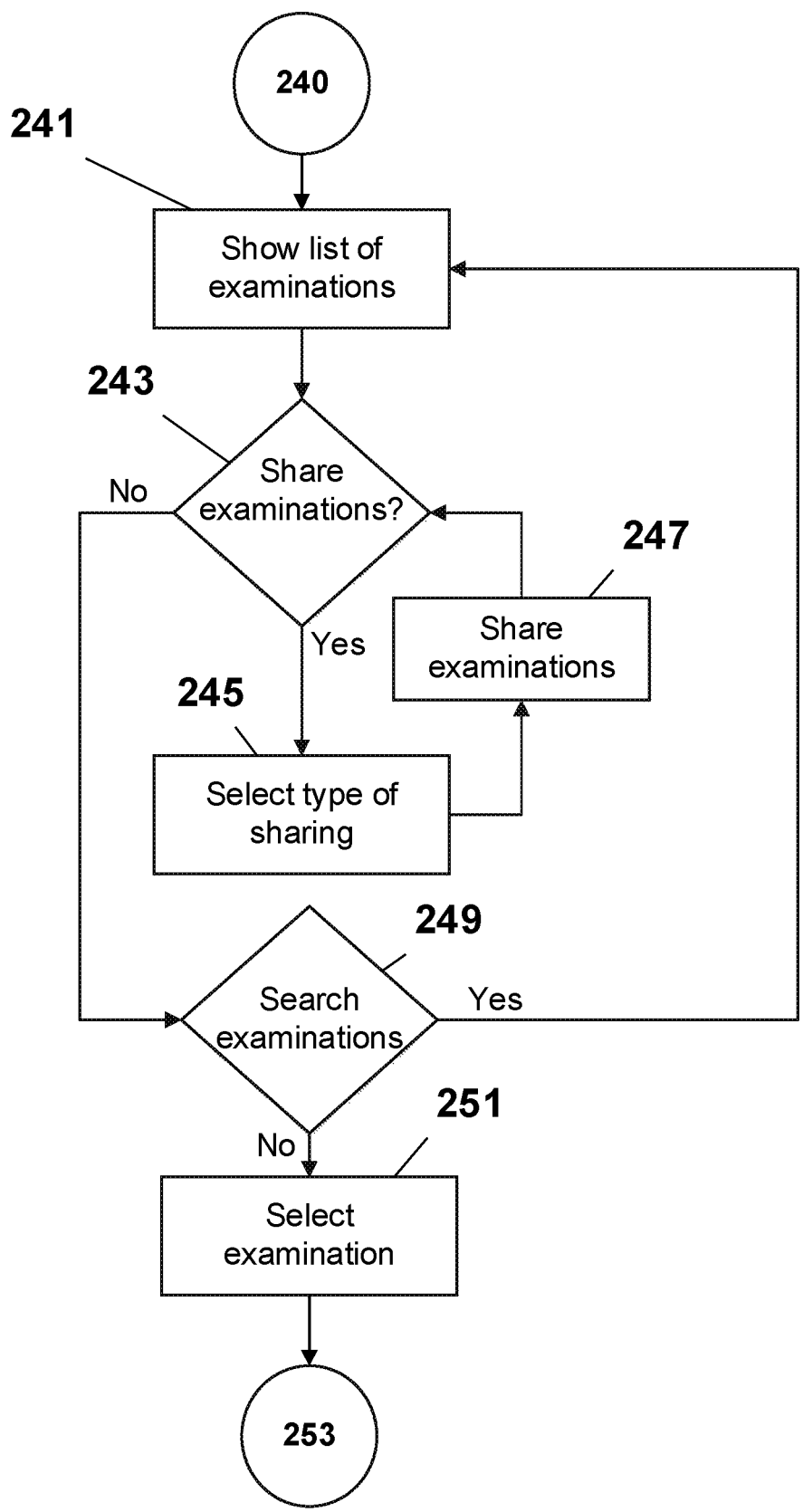
Figure 2D:
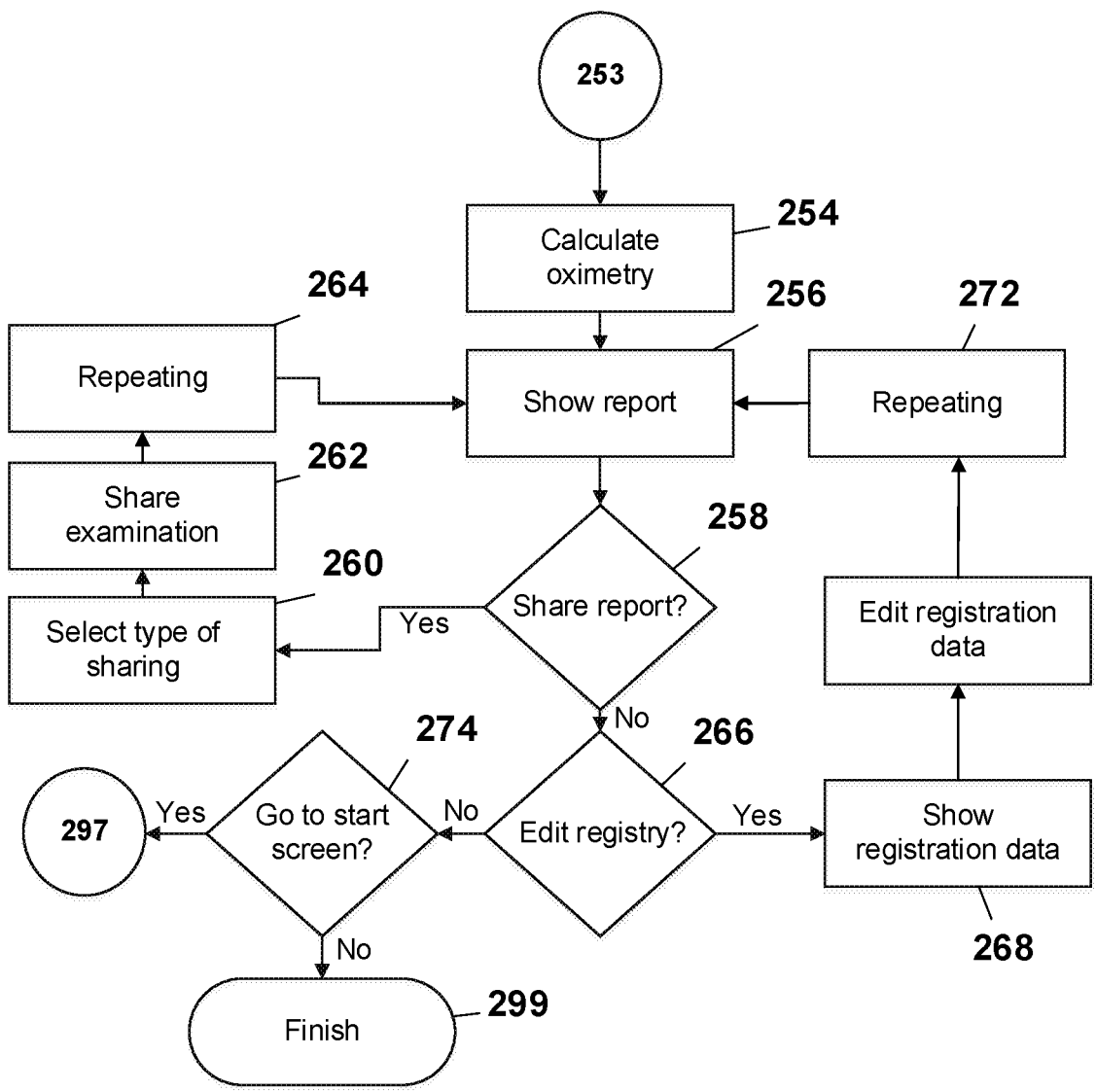

(52) U.S. Cl.
CPC ........... *A61B 5/6825* (2013.01); *A61B 5/6843* (2013.01); *A61B 2503/04* (2013.01); *A61B 2562/0233* (2013.01)

(56) References Cited

FOREIGN PATENT DOCUMENTS

| WO | 9962399 A1 | 12/1999 | | |
|---|---|---|---|---|
| WO | WO-2004001567 A2 | * | 12/2003 | ........... G06F 1/1632 |

\* cited by examiner

INTRODUCED TO ELECTROMEDICAL EQUIPMENT FOR AUTOMATED TRIAGE OF NEWBORN WITH POSSIBLE CONGENITAL HEART DEFECTS

This application claims priority benefit to Brazil Application No. 10 2016 018146 1, filed Aug. 4, 2016, which is hereby incorporated herein by reference in its entirety.

The present invention refers to improvements introduced to electromedical equipment object of Brazilian patent BR10 2012 012062-3, applied into automatic triage of newborn babies with purpose to detect possible congenital heart defects by means of little heart test, though improvements in its process and constructability, aiming to increase the number of users, increase the flexibility of test protocol, and change the usability in order to minimize errors, bringing advantages of higher testing speed, improved interface with user, better measurement quality, lower cost, higher usage versatility and lighter weight and smaller size of equipment.

The Brazilian patent request BR10 2012 012062-3 named Electromedical Equipment for Automated Triage of Newborn with Possible Congenital Heart Defects, filed by the same title owner of the present patent request, disclosed an equipment um that uses the pulse oximetry to identify the patients having heart defects/diseases, automatizing the conduction of little heart test in newborn patients, provided with a little heart test software preinstalled in its system, connectivity (Internet, Wi-Fi, Bluetooth, USB, Ethernet, serial, RS-232, printer, among others) in order to enable sharing or printing the examinations made, a keyboard (either physical or touchscreen) for allowing the health care professional to enter the patient identification data, a webcam, for enabling the patient photo is added to the examination report, and it may also have features such as single-dimension or bi-dimensional bar code reading, or communication systems via radio, or on-line systems for enabling the automatic insertion of patient data.

Although it has been a major evolution in the technology for detecting possible congenital heart defects through the little heart test, the equipment had some limitations, inconveniences and disadvantages that the inventors solved and ultimately resulted in the achievement of the improvements provided herein. The limitations, inconveniences and disadvantages observed were the long testing time, lack of usage flexibility in areas without internet, lack of flexibility in the working protocol, limitation in number of users, need for improved quality of measurement, equipment with large size and heavy weight, using a lot of space, and the high construction costs.

By searching both Brazilian and international patent databases, we found the following disclosures:

Patent published as document no. WO9962399, which disclosed a pulse oximeter that provides simultaneous measures, status of non-invasive oxygen and photoplethysmography in single and multiple locations. In particular, in multiple location, several parameters "pulse oximeter", or "stereo pulse oximeter" are simultaneously measured, arterial (SPA02) and venous oxygen saturation (SPV02) in any specific location, then generates a correspondent plethysmography waveform. A computing corresponding to negative arterial venous saturation is particularly advantageous to management of oxygen therapy. An induction mechanism having an active pulse unit generates a consistent pulsatile venous signal used for measuring venous blood. The stereo pulse oximeter also measures arterial oxygen saturation and forms photoplethysmography in several locations. A corresponding calculation of the delta arterial saturation and parameter comparison of photoplethysmography form among various locations is particularly advantageous for detecting and managing Persistent Pulmonary Hypertension of the Newborn (PPHN), Patent Ductus Arteriosus (PDA) and Coarctation of the Aorta (CoA).

United States patent US2010030040, which disclosed non-invasive methods and systems for measuring several blood components or analytes, such as glucose. In a realization form, it comprises a LED light source and superluminescent LEDs. The light source emits lights in minus wavelengths of approximately 1610 nm, at approximately 1640 nm, and approximately 1665 nm. In a realization form, the detector comprises a multitude of photo-detectors arranged into a special geometry consisting of a linear, straight chain of equal geometry substantially spaced, linear not equal geometry, equal geometry spaced, and a substantially large grade geometry.

United States patent US 2011082711, which disclosed a personal health organizer that enables patients and health care professionals to manage health data. The personal health organizer can be a portable device adapted to receive physiological reading data from a health-related data collection device or derive the data reading from signals acquired by a sensor, or module/platform software for executing even when it is configured to be executed in a general-purpose computing device, such as a mobile phone/computer. The personal health organizer integrates reading data with applications that aid and promote the health management, including reminders, alerts and tracking of health data. The data acquired from reading may be forwarded to the health care professionals for allowing them to provide feedback, such as warnings and diagnostics to the users. The personal health organizer may also support the integration of electronic health record via network computing for the medical data locally stored is automatically synchronized with remotely stored medical data.

"IMPROVEMENTS INTRODUCED TO ELECTROMEDICAL EQUIPMENT FOR AUTOMATED TRIAGE OF NEWBORN WITH POSSIBLE CONGENITAL HEART DEFECTS", object of the present patent, was developed to overcome the limitations, inconveniences and disadvantages of the technology disclosed in the patent request BR10 2012 012062-3 and other disclosures mentioned, by means of improvements introduced to the process performed by software and constructability of the power supply and electrical connections, which aimed to increase the number of users, increase flexibility of test protocol and change the usability in order to minimize errors, bringing advantages of higher testing speed, improved interface with user, better measurement quality, lower cost, higher usage versatility, and lighter weight and smaller size of equipment.

The current technologies provides the following technical issues that the present patent invention addressed:

1. Impossibility to use the equipment within areas not provided with internet, solved by the present invention by means of dedicated software, which enables using digital mediums, such as pendrive and external HD;

2. Impossibility to correct the examination in progress, solved by means of dedicated software with interface that enables redoing only a part of the examination;

3. Hampered examination time, solved by the present invention by means of dedicated software that provides configuration screen for selecting times;

4. Examination quality is compromised by the movements and sensibility of the patient, which affect its resolution, solved by means of dedicated software that provides algorithm that filters the patient motions, eliminating noises; and 5. Use of support as built-in electrical power supply and with male connectors connected to female connectors at the apparatus body require a large and heavy equipment, solved by means of construction simplification with small size connector, cable and power supply, making the apparatus self-supportive and compact.

The improvements introduced to the equipment, object of the present invention, were obtained after researches and developments of processes and hardware that aimed to resolve the problems identified in the equipment object of the patent request BR10 2012 012062-3 and that historically can be demonstrated in the following manner:

The product was being used in the market and some common difficulties were identified by the users. The main ones were:

1. Absence or difficulty to use the Wi-Fi in medical establishment. Some hospitals and clinics have no Wi-Fi or have a very strict safety protocol, such as firewalls, which prevents the apparatus from operating properly. The Wi-Fi is fundamental to enable saving or transferring the examination results into other equipment, such as a computer or digital medium;

2. High cost and space usage. A base is used to recharge the apparatus battery, which must be connected to the mains. An internal circuit converts into energy able for recharging the apparatus. Also, the base is used for supporting the apparatus, however, its dimensions are too large for and hospital environment and due to providing aesthetic function, it is costly; and 3. Long time to redo the test. The software implemented to conduct the Little Heart Test not allows redo the examination from a certain point in which some defect has been verified, therefore, it is necessary to restart the entire procedure. Furthermore, the oximetry reading times are fixed and cause dissatisfaction to some professionals having more experience with the examination and also to others that are less familiarized with it.

After a critical analysis meeting, the solutions to settle the reported problems were raised, and the following actions were taken:

1. For enabling to transfer the examination result without requirement to be connected to a Wi-Fi network, the option, the option "send examination result to pendrive" was added, thus, making it possible to save the examination result into a digital medium well consolidated in the market, not requiring to use a Wi-Fi network or any other communication means;

2. The base was replaced with a compact-sized metal support and an external battery charger. In order to use the charger, it was necessary coupling a power supply connector to the rear part of the apparatus. The replacement reduced both the cost and space used;

3. The user interface was modified to enable redoing only a part of the examination, avoiding the necessity to restart the entire procedure. The definition of times to measure the oximetry required during the examination are now configurable. This option meets both the needs of the most qualified professional, who requires a shorter time, and the beginner, who requires a longer period to conduct the measurement.

For a better understanding of the present patent, the following figures are found attached hereto:

FIG. 1., which shows the diagram with physical blocks of the equipment improved by the present patent, highlighting in dashed lines the items maintained from the previous equipment, and in full lines the items introduced in the present invention.

FIGS. 2A-D., which shows the block diagram of the process sequence performed by the dedicated software implemented into the equipment memory.

Figure 3:
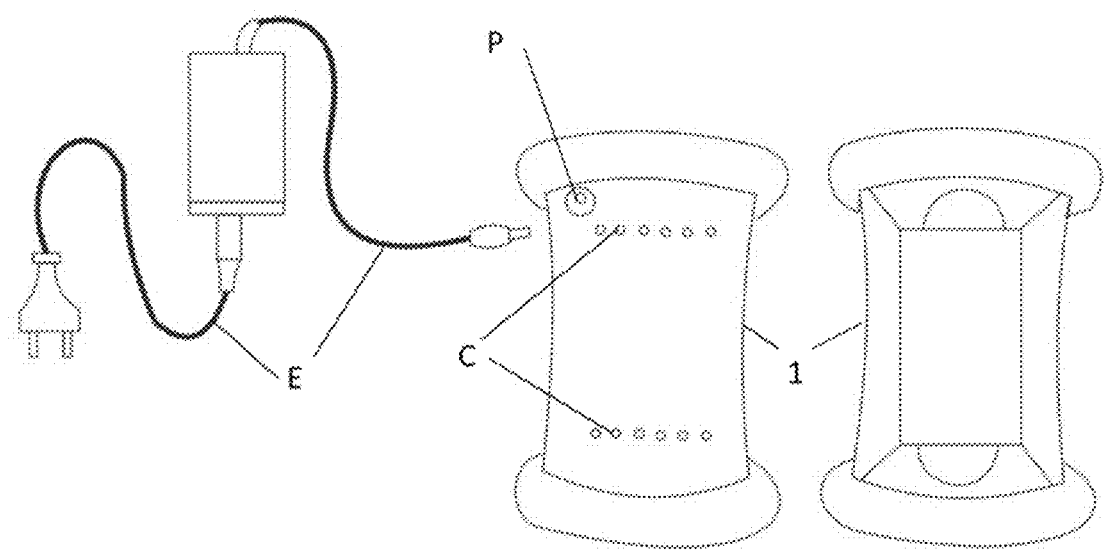

FIG. 3., which shows the rear view of the connector, cable, power supply and plug aligned with the equipment.

Figures 4, 5:
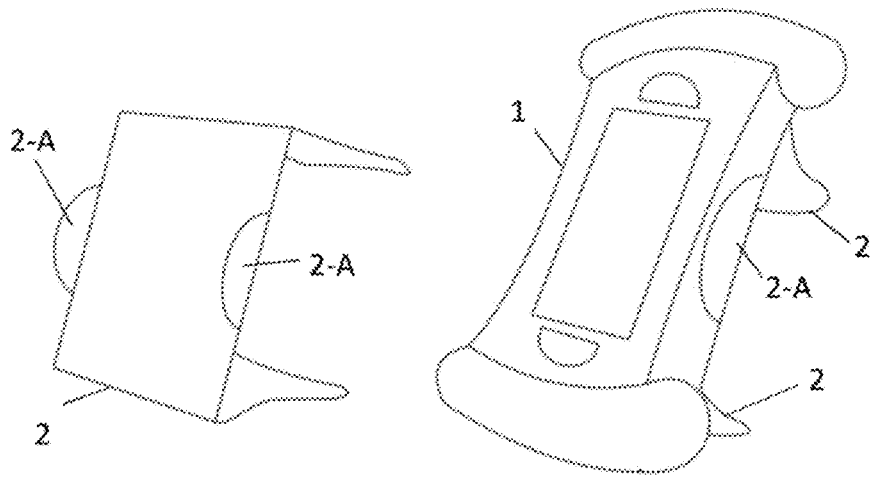

FIG. 4., which shows the front view of the improved equipment base.

FIG. 5., which shows the front view of the improved equipment mounted onto the base.

According to FIGS. 2A-D, the process 200 executed by the dedicated software (DS) is accomplished in the following sequence:

Start-up 202;
Start screen 204;
new examination ? 206; if yes, go to 210; if no, go to 208;
In 210, start examination 211;
measure right hand 213;
redo measurement ? 215; if yes, return to 213; if no, go to 217;
select right foot ? 217; if no, go to 219; if yes, go to 221;
measure left foot and go to 223;
measure right foot 221;
finish examination 223;
redo measurement ? 225; if yes, return to 217; if no, go to 227;
bind patient 227;
patient registered ? 229; if no, go to 231; if yes, go to 233;
register patients 229 and go to 237;
list patients 233;
select patient 239;
save examination 237 and go to 253;
list examinations ? 208; If yes, go to 240; if no, return to 204;
In 240, show list of examinations 241;
share examinations ? 243; if yes, go to 245; if no, go to 249;
search examination ? 249; if yes, return to 241; if no, go to 251;
select examination 251 and go to 253;
select type of sharing 245;
share examinations 247 and return to 241;
In 253, calculate oximetry 254;
show report 256;
share report ? 258; if yes, go to 260; if no, go to 266;
select type of sharing 260;
share examination 262 and repeat 264 by returning to 256;
edit registry ? 266; if yes, go to 268; if no, go to 274;
show registration data 268;
edit registration data 270 and repeat 272 by going to 256; and
go to start screen ? 274; if yes, go to 204, which is shown by pathway 297; if no, go to 256.

According to FIGS. 1, 3, 4 and 5, the improved equipment of the present patent is provided with apparatus (1) with power supply block (1-A) equipped with battery unidirectionally connected to blocks (1-B), (1-C), (1-D), (1-E), (1-G), (1-H), (1-I), (1-J), (1-K) and (1-L), and to processor (1-F), of sensor (S) placed onto patient (8) and bidirectionally connected to connector (1-B), with oximetry connector (1-B) unidirectionally connected to block (1-A) and bidirectionally connected to module (1-C), with oximetry module (1-C) unidirectionally connected to block (1-A) and bidirectionally connected to processor (1-F), with image capturing block (1-D) equipped with web cam unidirectionally connected to block (1-A) and to processor (1-F), with viewing block (1-E) equipped with touchscreen display with virtual keyboard unidirectionally connected to block (1-A)

and bidirectionally connected to processor (1-F) and to block (1-L), with processor (1-F) unidirectionally connected to block (1-A) and (1-D) and bidirectionally connected to memory (1-G) and to blocks (1-C), (1-D), (1-E), (1-H), (1-I), (1-J), (1-K) and (1-L), with memory (1-G) unidirectionally connected to block (1-A) and bidirectionally connected to processor (1-F), with communication block (1-H) equipped with Wi-Fi module bidirectionally connected to processor (1-F) and remotely communicating with cell phone (5), tablet (6) and printer (7), with communication block to USB-type digital medium (1-I) unidirectionally connected to block (1-A) and bidirectionally connected to processor (1-F), with Ethernet-type communication block (1-J) unidirectionally connected to block (1-A) and bidirectionally connected to processor (1-F), with RS232-type communication block (1-K) unidirectionally connected to block (1-A) and bidirectionally connected to processor (1-F), with Bluetooth®-equipped communication block (1-L) unidirectionally connected to block (1-A), bidirectionally connected to processor (1-F) and remotely, bidirectionally connected to cell phone (5), tablet (6) and printer (7), with introduced improvements of dedicated software (DS) implemented in memory (1-G), georeference block (1-M) bidirectionally connected to processor (1-F), from pendrive (3) unidirectionally connected to communication block with digital medium (1-I), external HD (4) unidirectionally connected to communication block with digital medium (1-I), from energy and supply assembly (E) equipped with DC02215V J4 connector, cable and power supply, plug (P) positioned at rear panel of the apparatus (1), internal and external connections (C) with magnets arranged into two rows at rear part of the apparatus (1), of "C"-shape metallic base (2) with two front flanges (2-A) and attachable by magnetism at the rear panel of the equipment.

The equipment mounting for use is done in the following sequence:

1. Connect the power supply cable to the apparatus and the power grid. This step may be bypassed if the battery has sufficient charge to supply the apparatus;

[068] 2. Press the power-on button for 2 seconds. The apparatus will switch on;

3. After the apparatus is started, you must connect the oximetry sensor in the equipment to the patient; and 4. Perform the test as the following protocol:

The test conduction by the user follows the protocol below:

A. Start test: in the Little Heart Test application start screen, click on "New Examination";

B. Position the sensor: place the sensor in the right hand of the baby and wait until the reading starts, when finishing the hand reading, repeat the previous process in one of the baby's feet;

C. Baby profile: First examination: Add the baby profile to the test, click on "Add patient" and choose the option "New Registry"; Second examination: Add the baby profile to the test, click on "Add patient" and choose the option to bind the test to an profile already "Registered" then save the test:

D. Profile report: the test "Report" displays the personal information of the baby that may be edited, the results of measurements and sharing option appear below; and E. When the result is abnormal, follow the instructions displayed in the item "Result" and finish 299.

The invention claimed is:

1. An apparatus (1) for electromedical equipment for automated triage of a new born possibly having a congenital heart defect, comprising a power supply block (1-A) equipped with a battery unidirectionally connected to an oximetry connector (1-B), a oximetry module (1-C), an image capturing block (1-D), a viewing block (1-E), a memory (1-G), a communication block (1-H), a Universal Serial Bus digital medium (1-I), an Ethernet communication block (1-J), an RS232 communication block (1-K) and a communication block (1-L), and to a processor (1-F), of a sensor (S) configured to be placed onto a patient (8) and bidirectionally connected to the oximetry connector (1-B), with the oximetry connector (1-B) unidirectionally connected to the power supply block (1-A) and bidirectionally connected to the oximetry module (1-C), with the oximetry module (1-C) unidirectionally connected to the power supply block (1-A) and bidirectionally connected to the processor (1-F), with the image capturing block (1-D) equipped with a web cam unidirectionally connected to the power supply block (1-A) and to the processor (1-F), with the viewing block (1-E) equipped with a touchscreen display with a virtual keyboard unidirectionally connected to the power supply block (1-A) and bidirectionally connected to the processor (1-F) and to the communication block (1-L), with the processor (1-F) unidirectionally connected to the power supply block (1-A) and the image capturing block (1-D) and bidirectionally connected to the memory (1-G) and to the oximetry module (1-C), the image capturing block (1-D), the viewing block (1-E), the communication block (1-H), the Universal Serial Bus digital medium (1-I), the Ethernet communication block (1-J), the RS232 communication block (1-K) and the communication block (1-L), with the memory (1-G) unidirectionally connected to the power supply block (1-A) and bidirectionally connected to the processor (1-F), with the communication block (1-H) equipped with a wireless local area networking module bidirectionally connected to the processor (1-F) and remotely communicating with a cell phone (5), a tablet (6) and a printer (7), with communication block to the Universal Serial Bus digital medium (1-I) unidirectionally connected to the power supply block (1-A) and bidirectionally connected to the processor (1-F), with the Ethernet communication block (1-J) unidirectionally connected to the power supply block (1-A) and bidirectionally connected to the processor (1-F), with the RS232 communication block (1-K) unidirectionally connected to the power supply block (1-A) and bidirectionally connected to the processor (1-F), with the communication block (1-L) unidirectionally connected to the power supply block (1-A), bidirectionally connected to the processor (1-F) and remotely, bidirectionally connected to cell phone (5), tablet (6) and printer (7), with introduced improvements, characterized as, the memory (1-G) has stored thereon dedicated software (DS) comprising instructions which, when executed by the processor (1-F), performs a process, georeference block (1-M) bidirectionally connected to the processor (1-F), a pendrive (3) unidirectionally connected to communication block with the Universal Serial Bus digital medium (1-I), an external hard drive (4) unidirectionally connected to communication block with the Universal Serial Bus digital medium (1-I), an energy and supply assembly (E) equipped with a connector, cable and a power supply, a plug (P) positioned at a rear panel of the apparatus (1), internal and external connections (C) with magnets arranged into two rows at a rear part of the apparatus (1), a "C"-shape metallic base (2) with two front flanges (2-A) and attachable by magnetism at the rear panel of the equipment, wherein the process is performed in the following sequence:

a) prompting, by the processor, a user to start-up;
a1) displaying, on the touchscreen display, a start screen;
a2) prompting, on the start screen, the user if the user will conduct a new examination, and when the user answers yes on the touchscreen,
   b) prompting, on the touchscreen display, the user to start examination;
   b1) measuring via the sensor (S) connected to the patient's right hand;
   b2) prompting, on the touchscreen display, the user if the user will redo measurement, and
      when the user answers yes on the touchscreen, to repeat step b1) and b2);
      or when the user answers no on the touchscreen,
   b3) prompting, on the touchscreen display, the user if the user will select right foot, and
      when the user answers no, b3a) measuring via the sensor (S) connected to the patient's left foot;
      or when the user answers yes, b3b) measuring via the sensor (S) connected to the patient's right foot;
   b4) prompting, on the touchscreen display, the user if the user will finish examination by:
   b5) prompting, on the touchscreen display, the user if the user will redo measurement, and
      when the user answers yes, repeating steps b3), b4), and b5);
      or when the user answers no,
   b6) prompting, on the touchscreen display, the user if the user will bind the patient by:
   b7) prompting, on the touchscreen display, the user if the patient is registered, and
      when the user answers no, b7a) prompting the user to register the patient;
      or when the user answers yes, b7b) listing, on the touchscreen, the patient, and b7b1) selecting the patient; and
   b8) saving the examination data;
   d) calculating, via the processor, oximetry;
   d1) showing, on the touchscreen display, a report;
   d2) prompting, on the touchscreen display, the user if the user will share the report, and
      when the user answers yes, d2a) prompting, on the touchscreen display, the user to select a type of sharing, d2a1) sharing examination d2a2) repeating step d1) and d2);
      or when the user answers no,
   e) prompting, on the touchscreen display, the user to edit a registry, and
      when the user answers yes, e1) showing, on the touchscreen display, registration data, e2) prompting, on the touchscreen display, the user to edit registration data and e3) repeating steps d1), d2), and e);
      or when the user answers no,
   f) prompting, on the touchscreen display, if the user will go to the start screen,
      when the user answers yes, repeat steps a1), a2), b), b1), b2), b3), b3a) or b3b), b4), b5), b6), b7), b7a) or both b7b) and b7b1), b8), d), d1), d2), e), and f); or
      when the user answers no, displaying, on the touchscreen display, the exam results which include the calculated oximetry;
or
a3) when prompting, on the touchscreen display, if the user will list examinations, and when the user answers yes,
   c) showing, on the touchscreen display, a list of examinations;
   c1) prompting, on the touchscreen display, if the user will share examinations, and
      when the user answers yes, c1b) selecting a type of sharing, c1b1) sharing examinations, repeating steps c) and c1);
      or when the user answers no, c1a) prompting, on the touchscreen display, if the user will search examination, and
      either when the user answers yes, repeating steps c) and c1);
   c1a1) selecting, by the user, examination;
   d) calculating, via the processor, oximetry;
   d1) showing, on the touchscreen display, a report;
   d2) prompting, on the touchscreen display, the user if the user will share the report, and
      when the user answers yes, d2a) prompting, on the touchscreen display, the user to select a type of sharing, d2a1) sharing examination d2a2) repeating step d1) and d2),
      or when the user answers no,
   e) prompting, on the touchscreen display, the user to edit a registry, and
      when the user answers yes, e1) showing, on the touchscreen display, registration data, e2) prompting, on the touchscreen display, the user to edit registration data and e3) repeating steps d1), d2), and e),
      or when the user answers no,
   f) prompting, on the touchscreen display, if the user will go to the start screen,
      when the user answers yes, repeat steps a1), a2), a3), c), c1), c1a), c1a1), d), d1), d2), e), and f); or
      when the user answers no, displaying, on the touchscreen display, the exam results which include the calculated oximetry.

2. The apparatus according to claim 1, wherein the touchscreen display is configured to display a configuration screen for selecting the examination times.

3. The apparatus according to claim 1, wherein the sensor (S) is configured to detect the patient's movements.

* * * * *